(12) United States Patent
Ellman et al.

(10) Patent No.: US 6,905,496 B1
(45) Date of Patent: Jun. 14, 2005

(54) RF ELECTROSURGERY CRYOGENIC SYSTEM

(76) Inventors: Alan G. Ellman, 1135 Railroad Ave., Hewlett, NY (US) 11557; Jon C. Garito, 1135 Railroad Ave., Hewlett, NY (US) 11557

( * ) Notice: Subject to any disclaimer, the term of this patent is extended or adjusted under 35 U.S.C. 154(b) by 172 days.

(21) Appl. No.: 10/284,539

(22) Filed: Nov. 1, 2002

(51) Int. Cl.[7] .............................................. A61B 18/18

(52) U.S. Cl. .................. 606/41; 607/101; 607/102

(58) Field of Search ............... 606/32–50; 607/96–122

(56) References Cited

U.S. PATENT DOCUMENTS

| 6,413,255 B1 * | 7/2002 | Stern ........................... 606/41 |
| 6,749,624 B2 * | 6/2004 | Knowlton ................... 607/104 |
| 2002/0151887 A1 * | 10/2002 | Stern et al. .................. 606/41 |

* cited by examiner

*Primary Examiner*—Roy D. Gibson

(57) ABSTRACT

An electrosurgical system that is capable of performing an electrosurgical procedure while cooling the surgical site before, during or after the surgical procedure. To a handpiece or to an electrosurgical generator may be mounted a pressurized cryogenic fluid container together with means associated with the handpiece for directing the cryogenic fluid when released from the container at the surgical site, and means for activating the valve of the container to release the pressurized fluid from the container.

20 Claims, 4 Drawing Sheets

RF ELECTROSURGERY CRYOGENIC SYSTEM

This invention relates to Radio Frequency (RF) electrosurgery for carrying out various surgical procedures. In particular, it relates to an electrosurgical system that is capable of performing an electrosurgical procedure while cooling the surgical site before, during or after the surgical procedure.

BACKGROUND OF THE INVENTION

U.S. Pat. No. 5,647,871, whose contents are hereby specifically incorporated by reference, describes a cooled electrosurgical system in which the electrosurgical electrode is provided with an internal cavity in which a cooling medium such as water can be circulated. The cooling medium is confined to the electrode interior at the surgical site such that the cooling medium does not contact the tissue being treated.

A disadvantage of such a device is that a complicated, and thus expensive, custom handpiece and custom electrodes are necessary, not counting the expensive auxiliary units for supplying and removing the circulating fluid.

SUMMARY OF THE INVENTION

An object of the invention is an RF electrosurgical system that is capable of performing an electrosurgical procedure while cooling the surgical site before, during or after the surgical procedure.

Another object of the invention is a cooled RF electrosurgical system that is easily adapted to use with a standard handpiece and standard electrosurgical electrodes.

Briefly stated, the cooled RF electrosurgical system in accordance with a feature of the invention can use a standard handpiece and standard electrosurgical electrodes for providing the common electrosurgical procedures which is combined with a source of cryogenic fluid whose operation can be controlled by the surgeon to cool the surgical site independently of application of the RF energy.

In a preferred embodiment, to the handpiece is mounted a pressurized cryogenic fluid container together with means for directing the cryogenic fluid when released from the container at the surgical site, and means for activating the valve of the container to release the pressurized fluid from the container.

The cooled RF electrosurgical system in accordance with another feature of the invention employs an electromagnetic device to activate the container valve, with a separate fingerswitch mounted on or in the handpiece to operate the electromagnetic device. In this way, it is possible for the surgeon to cool the surgical site not only during the electrosurgical procedure but if desired before and after the electrosurgical procedure has been carried out.

The advantages of the invention over the referenced prior art patent, apart from its obvious simplicity and low cost, is that the cryogen fluid is absorbed by the target tissue at the surgical site and within seconds the cryogenic fluid evaporates after impinging on the target site. Thus, there is no impediment to the RF energy flow from the electrode to the target tissue thus allowing the ordinary smooth movement of the electrode cutting through the tissue. Another important advantage is that the system is easily adapted to accommodate standard handpieces that can use standard electrodes, instead of being limited to hollow sealed electrodes as in the patented device.

Preferably, the electrosurgical instrument of the invention works best with relatively high-frequency RF electrosurgical currents in excess of 1.5 MHz, preferably in the range of 1.5–4 MHz, as we believe that using electrosurgical currents in the MHz range also causes relatively low tissue temperatures avoiding possible damage to adjacent tissue.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described the preferred embodiments of the invention.

DETAILED DESCRIPTION OF THE PREFERRED EMBODIMENTS

The reader is directed to the referenced prior patent which will assist in understanding the improvements offered by the present application. Conventional electrosurgical apparatus or generators can be used with systems of the invention, but it is preferred to use low-power electrosurgical apparatus. Such apparatus is available from Ellman International of Hewlett, NY as Model IEC50. The latter has the advantage that it generates RF electrosurgical currents in the MHz range, specifically, about 1.5–4 MHz, which we prefer for their less damaging effect on neighboring tissue.

In the application of the invention, a pressurized can of a commercially-available cryogenic fluid is used. The cryogenic fluid can be any of the well-known cryogenic fluids which when maintained under pressure remain in liquid condition but when released into the environment produce a gas or vapor at a very low temperature, such as $-20°$ or $-40°$ which quickly evaporates, but which has a quick cooling effect on tissue. Physicians have been using such pressurized cryogenic fluids for many years for, for example, destroying skin lesions by freezing and killing the tissue cells. An object of the invention is to combine a pressurized can of cryogenic fluid with an electrosurgical handpiece such that the physician, before, during, or subsequent to an electrosurgical procedure can cool down the tissue at the surgical site.

Figure 1:
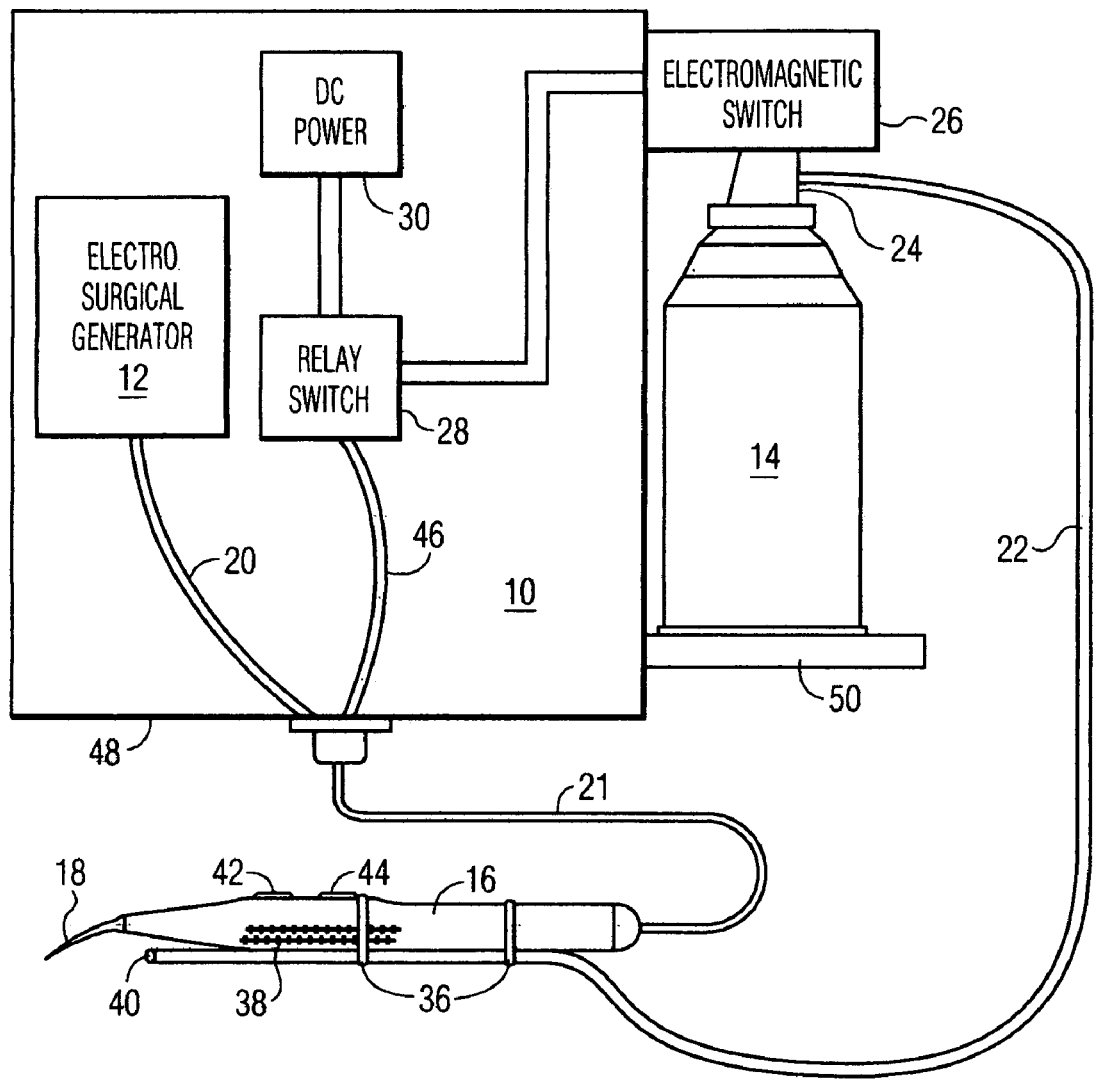
FIG. 1 is a block diagram of one form of a cooled RF electrosurgical system in accordance with the invention.

With reference to FIG. 1, a cooling electrosurgical system 10 according to the invention comprises several major components including an electrosurgical generator 12, a cooling source in a pressurized container 14, an electrosurgical handpiece 16 comprising at a working end an electrode 18, and means for activating the electrosurgical generator for performing a radiofrequency procedure and for activating the pressurized container to cool the target tissue. The electrosurgical generator 12 may be of the conventional type and the attached electrode 18 atached to the handpiece 16 may also be one of many differently shaped well-known electrodes such as needles, balls, loops, curettes, scalpel blades, etc. To perform an electrosurgical tissue procedure, preferably using RF energy, the electrosurgical generator 12 delivers radiofrequency energy via a cable connector 20 and a common cable connector 21 to the electrode handpiece 16. In this way the energy is delivered to the electrode 18 which will typically contact the tissue for the surgical procedure. Heat is generated in the tissue because of the RF energy. A cooling agent may be needed for reducing the tissue damage from any excessive heat caused during the procedure by the RF energy. The source of cryogenic fluid in the cooling container 14 delivers the cooling agent to the target tissue to cool the tissue before, during, and/or after the procedure whenever it is felt necessary or desirable by the surgeon. The cryogenic fluid is delivered via a flexible tube 22 attached to a spout or other outlet 24 for the fluid on the container.

Figure 9:
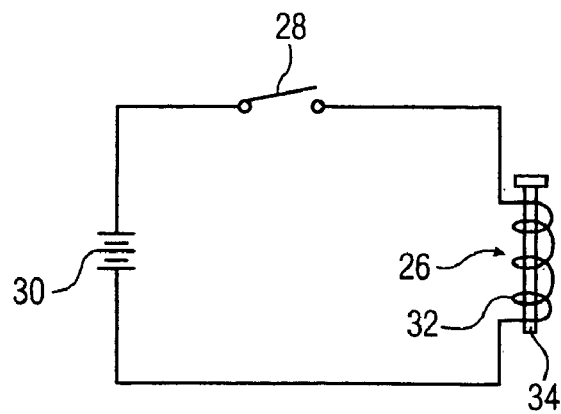
FIG. 9 is a circuit diagram of one form of the system of the invention.

An electromagnetic switch such as a solenoid 26 is mounted on top of the container 14 which typically houses a valve (not shown) operable by a user to cause pressurized fluid to be discharged from the spout 24. The electromagnetic switch is connected to a relay switch 28, which is in turn connected to a source of DC power 30. The circuit is relatively simple, as schematically illustrated in FIG. 9. A DC low voltage solenoid 26 is preferably used as the electromagnetic switch 26, and comprises a coil 32 and a magnetic core or plunger 34. When the relay switch 28 is closed, DC power activates the solenoid 32 which drives the plunger downward. The typical pressurized container contains a valve that operates when depressed, which is the function performed by the bottom end of the plunger 34. While the relay switch is closed, the pressurized cooling fluid is discharged from the pressurized container. As will be observed, the discharge tube 22 has a distal portion which is attached to the body of the electrosurgical handpiece 16 in any convenient way. FIG. 1 shows the use of clips or ties 36 and Velcro 38, but other attachment means are equally suitable. The open tube end 40 that serves as the outlet of the cryogenic fluid is located adjacent the electrode 18 and pointing in the same direction. The tube mounting 36, 38 preferably allows the position of the tube outlet to be adjusted by the surgeon so as to direct the cooling medium at the target site from the distance deemed desirable, to control the degree of cooling.

While the power to operate the electromagnetic switch 26 can be derived from the electrosurgical generator 12, this would require accessing the power supply inside the electrosurgical generator housing. By providing a separate DC power source, such as a battery 30, then the assembly of relay switch 28 and power source 30 can be packaged separately and merely attached to or be positioned adjacent the generator housing. It will also be evident to those persons of ordinary skill in the art that other circuits and circuit components can readily be devised to accomplish the same results, and they are also deemed within the scope of the invention.

Figure 2:
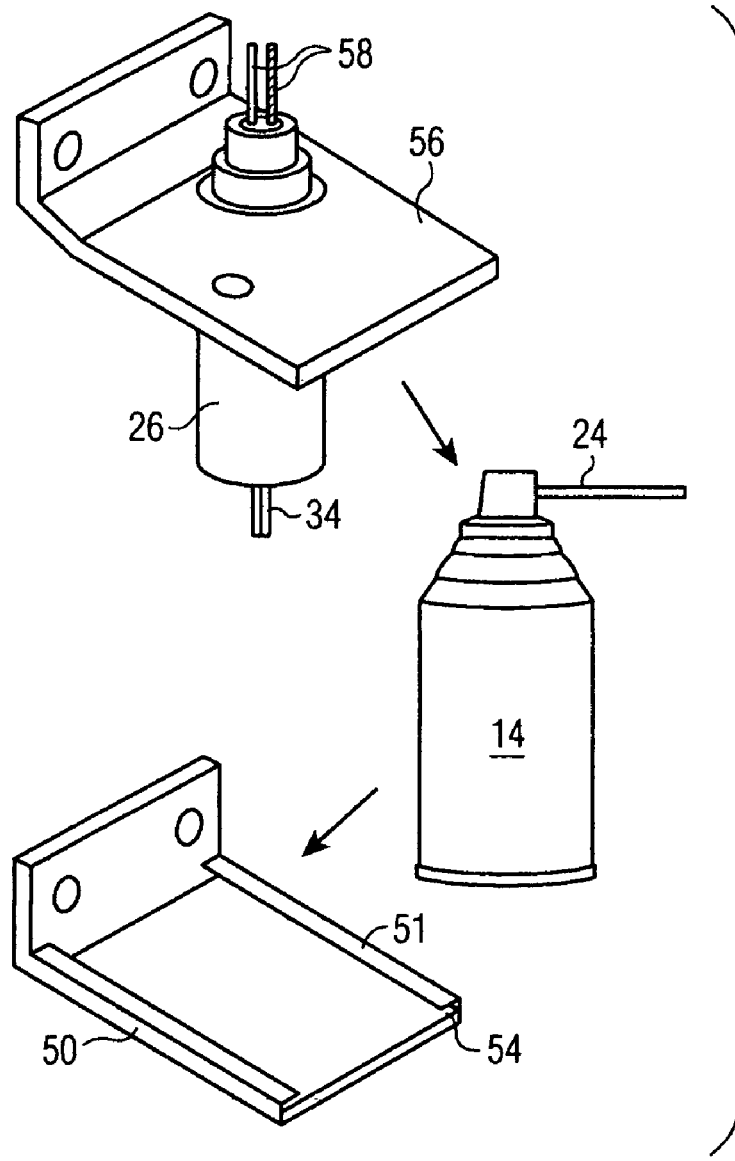
FIG. 2 shows, in perspective, one way in which components of the system can be assembled.

In the preferred embodiment, a handpiece 16 with two button switches 42, 44 is employed. This can be readily obtained from various suppliers. A first button switch 42 is used in the normal way to activate the electrosurgical generator 12 and is thus wired to the latter via the cable connector 20 and a separate part of the common cable connector 21. The second button switch 44 is used to activate the relay switch 28 and is thus separately and independently wired to the latter via a cable connector 46 and a separate part of the common cable connector 21. Thus, the RF energy and the cooling medium can be separately and independently supplied to the surgical site, or if the surgeon prefers, by pressing both buttons simultaneously both the RF energy and the cooling medium can be supplied together to the surgical site. While it is possible to interconnect the two circuits so that a single button press will simultaneously apply both electrosurgical currents and the cooling medium to the target site, it is preferred that separate circuits are used as it offers more choices to the surgeon so that the target site can be cooled before, during or subsequent to the actual application of the electrosurgical currents. As illustrated in FIG. 1, if desired, the electrosurgical generator 12, relay switch 28 and DC power source 30 can also be mounted within a common housing 48 that allows access to the generator controls. In the latter case, the pressurized container 14 can be conveniently mounted on that housing 48. One way, not to be deemed limiting, is illustrated in FIG. 2. A support bracket 50 can be mounted to the side of the housing 48, and the pressurized can 14 can be supported on a surface of the bracket 50. As shown, a rim 51 forming a slot 54 is provided on the bracket support surface and the pressurized container, which typically contains a rim at its bottom, can be slid into the slot 54. The electromagnetic switch can similarly be mounted to the housing side by a bracket 56 (not shown in FIG. 1). FIG. 2 also shows the solenoid plunger 34 and two wires 58 that would be connected to the relay switch 28.

Figure 3:
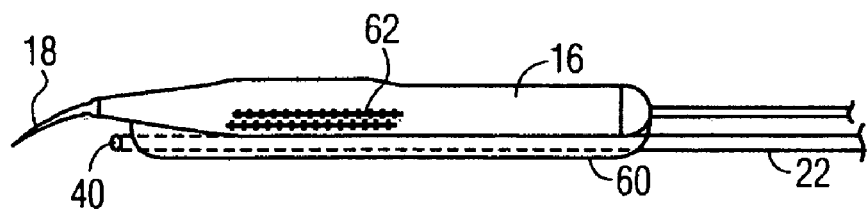
FIG. 3 shows a variant of one component of the system of the invention.

FIG. 3 shows a variant wherein the a hollow support 60 can be made integral with the handpiece housing, or attached by, for example, Velcro 62 to the handpiece housing. The cryogenic fluid discharge tube 22 can then be slid into the hollow support 60 and secured therein in any convenient manner. This construction allows the tube to be replaced after each surgical procedure.

Figure 4:
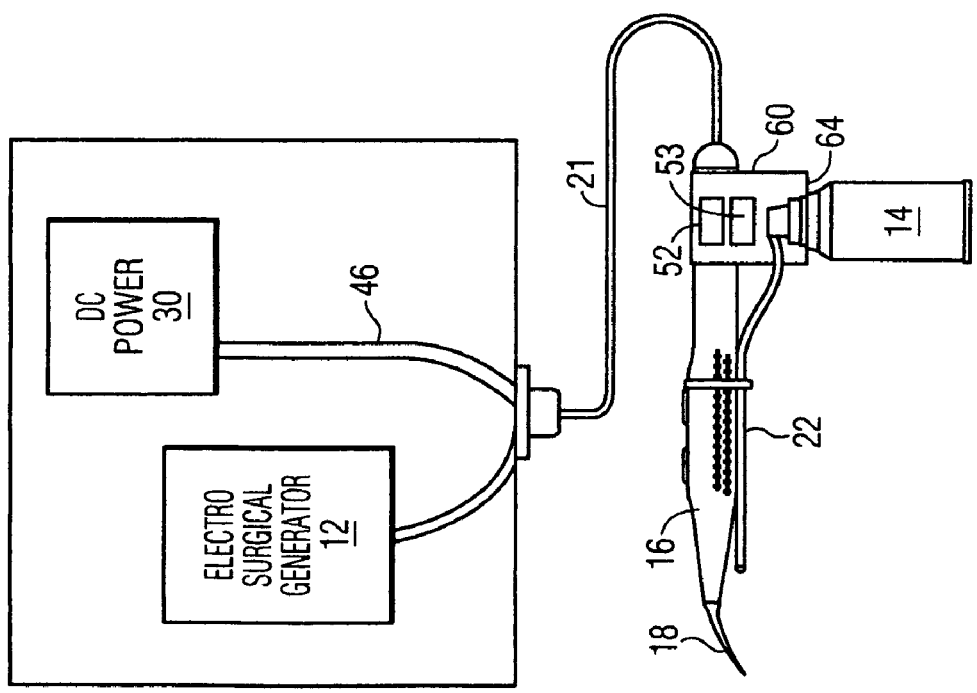

FIG. 4 shows still another variant, wherein an electromagnetic switch 53 and a relay switch 52 are both mounted on top of a pressurized container 14, which in this case is of the miniature type, as the combined assembly 14, 52, 53 can now be mounted directly on the handpiece 16, at the end opposite the working end that contains the electrode 18. In this case, the DC power source 30 is separately packaged. However, the latter, if light enough, can also be mounted to the handpiece or the pressurized container and connected by a connector to the cable 46.

Figure 6:
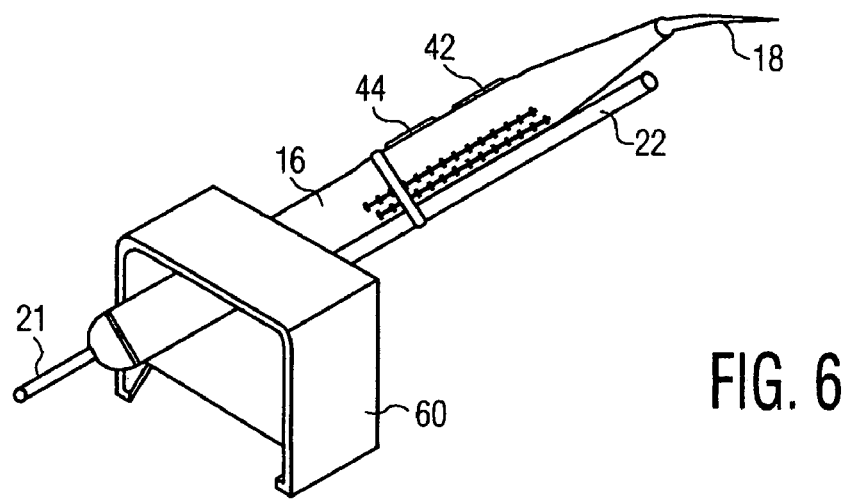
FIGS. 6–8 are perspective views showing one way in which components of the FIG. 4 embodiment can be assembled.
Figure 7:
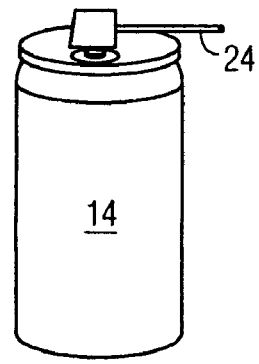
Figure 8:
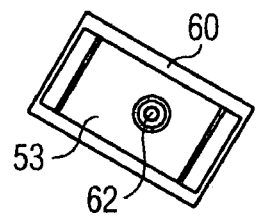

FIGS. 6–8 illustrate one way of accomplishing the FIG. 4 arrangement. FIG. 7 shows the pressurized container 14 with its discharge spout 24. FIG. 6 shows a bracket 60 for mounting at the rear of the handpiece 16. Inside the bracket 60, but not shown in detail in FIG. 6 is the relay switch 52 and below it the electromagnetic switch 53. FIG. 8 is a bottom view of the assembly of FIG. 6 showing the electromagnetic switch 53 and its solenoid plunger 62 in a position to activate the pressurized container valve when activated.

Figure 5:
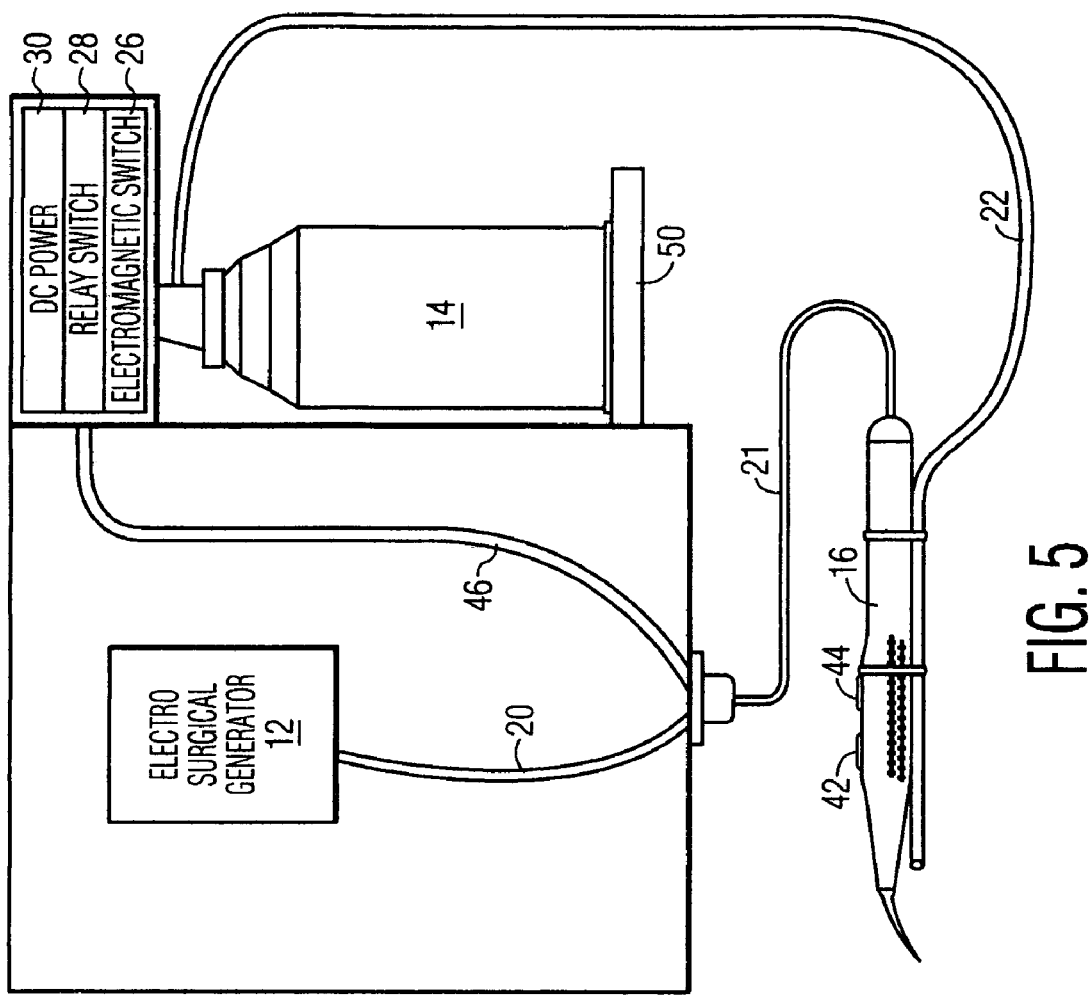
FIGS. 4 and 5 are block diagrams of two more variants of the invention.

FIG. 5 shows still a further embodiment wherein the pressurized container 14 is mounted as by a bracket 50 to the electrosurgical generator housing and the assembly of the electromagnetic switch 26, relay switch 28, and power source 30 are all mounted in any convenient manner on top of the pressurized container.

In all the embodiments illustrated, the arrangement is such that the cooling source pressure valve is right beneath the electromagnetic switch, so that upon activation of the relay switch power generates a mechanical force within the electromagnetic switch 13 that will press down on the cooling source valve button to eject cryogenic fluid that will flow through the tube 22 and aimed at the target tissue. The cooling source spray on the target tissue reduces the tissue temperature. The relay switch is controlled by a fingerswitch which is a part of the electrode handpiece and right at the finger tip of the surgeon.

The FIG. 4 embodiment shows that the cooling source container and its controlling system can be combined to become a separate portable unit 60. Then, the portable unit 60 can be attached to any model of the radiofrequency surgical generator for application of the cooling medium. The unit 60 is readily mounted on the miniature pressurized container by means of parallel rails 64 shown schematically beneath the control compartment 60. Another advantage of this arrangement is that it reduces the length of the tube 22 to obtain a quicker cooling response.

While the preferred embodiment uses a fingerswitch on the handpiece to activate the pressurized cryogenic fluid container so that both control of the electrosurgical currents and discharge of the cryogenic fluid are at the fingers of the surgeon, it will be appreciated that it is also possible to use a foot switch connected to the relay switch to activate the latter to discharge cryogenic fluid, in which case if a 2-button handpiece were employed, the second button can be employed to apply suction or irrigating fluid or a different electrosurgical current to the surgical site. Similarly, a foot switch can be used to activate the electrosurgical generator, and a handpiece fingerswitch used to supply the cooling medium.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. An electrosurgical system that is capable of performing an electrosurgical procedure while cooling the surgical site before, during or after the surgical procedure, comprising:
    a) a handpiece for connection to an electrosurgical generator, said handpiece being capable of receiving an electrosurgical electrode for applying electrosurgical currents to the surgical site when the electrosurgical generator is energized,
    b) a pressurized cryogenic or coolant fluid container having activating means for discharging cryogenic or coolant fluid from the pressurized fluid container when activated,
    c) fluid delivery means mounted on the outside of the handpiece and connected to the container for directing the fluid when discharged from the container directly to the tissue at the surgical site,
    d) first means associated with the handpiece for energizing the electrosurgical generator,
    e) second means associated with the handpiece for activating the activating means of the container to discharge the fluid from the container such that it is delivered to the fluid delivery means and thus applied directly to the surgical site to cool same.

2. An electrosurgical system as claimed in claim 1, wherein the first and second means operate separately and independently.

3. An electrosurgical system as claimed in claim 2, wherein the first and second means comprise first and second finger switches, respectively, on the handpiece, the first fingerswitch being connected to the electrosurgical generator, the second fingerswitch being connected to the activating means on the container.

4. An electrosurgical system as claimed in claim 3, wherein the activating means is mounted on the container.

5. An electrosurgical system as claimed in claim 4, further comprising a circuit connected to the activating means and the second fingerswitch for activating the former when the latter is activated.

6. An electrosurgical system as claimed in claim 5, wherein the circuit comprises a source of DC power and a relay switch, the second fingerswitch when activated closing the relay switch and applying DC power to operate the activating means.

7. An electrosurgical system as claimed in claim 6, wherein the activating means comprises an electromagnetic switch.

8. An electrosurgical system as claimed in claim 7, wherein the DC power source and the relay switch are separate from the pressurized fluid container.

9. An electrosurgical system that is capable of performing an electrosurgical procedure while cooling the surgical site before, during or after the surgical procedure, comprising:
    a) a handpiece for connection to an electrosurgical generator, said handpiece being capable of receiving an electrosurgical electrode for applying electrosurgical currents to the surgical site when the electrosurgical generator is energized,
    b) a pressurized cryogenic or coolant fluid container having activating means for discharging cryogenic or coolant fluid from the pressurized fluid container when activated,
    c) fluid delivery means associated with the handpiece and connected to the container for directing the fluid when discharged from the container to the tissue at the surgical site,
    d) first means associated with the handpiece for energizing the electrosurgical generator,
    e) second means associated with the handpiece for activating the activating means of the container to discharge the fluid from the container such that it is delivered to the fluid delivery means and thus applied to the surgical site to cool same,
    f) the first and second means operating separately and independently, the first and second means comprising first and second finger switches, respectively, on the handpiece, the first fingerswitch being connected to the electrosurgical generator, the second fingerswitch being connected to the activating means on the container,
    g) the activating means comprising an electromagnetic switch and being mounted on the container,
    h) circuits connected to the activating means and the second fingerswitch for activating the former when the latter is activated, the circuits comprising a source of DC power and a relay switch, the second fingerswitch when activated closing the relay switch and applying DC power to operate the activating means,
    i) the DC power source and the relay switch being separate from the pressurized fluid container, the relay switch being mounted on the pressurized cryogenic fluid container.

10. An electrosurgical system as claimed in claim 5, further comprising a housing containing at least one of the electrosurgical generator and activating means, and means for mounting the pressurized fluid container on the housing.

11. An electrosurgical system as claimed in claim 9, further comprising means for mounting the pressurized fluid container containing the relay switch and electromagnetic switch on the handpiece.

12. An electrosurgical system as claimed in claim 1, wherein the fluid in the pressurized fluid container is a cryogenic fluid or a gel, and the fluid delivery means comprises a tube and connected at one end to the pressurized fluid container and mounted to the handpiece such that the other end of the tube faces in the same direction as the electrode.

13. In combination:
(A) electrosurgical apparatus capable of generating electrosurgical currents,
(B) a handpiece having at least a first fingerswitch,
(C) an electrode mounted to the handpiece,
(D) a pressurized cryogenic fluid container,
(E) discharge means connected to the pressurized cryogenic fluid container for causing discharge of cryogenic fluid from the container,
(F) cryogenic fluid delivery means connected to the pressurized cryogenic fluid container and mounted on the outside of the handpiece and directed such that cryogenic fluid when discharged is applied directly to the surgical site,
(G) first means for connecting the first fingerswitch to the electrosurgical apparatus such that when the first fingerswitch is activated electrosurgical currents are applied by the electrode to a surgical site to carry out a surgical procedure,
(H) a second switch,
(I) second means for connecting the second switch to the discharge means such that cryogenic fluid released from the pressurized cryogenic fluid container will flow to the fluid delivery means for being directly applied to the surgical site.

14. The combination of as claimed in claim 13, wherein the first and second means operate separately and independently.

15. The combination as claimed in claim 14, wherein the first and second means comprise first and second finger switches, respectively, on the handpiece, the first fingerswitch being connected to the electrosurgical apparatus, the second fingerswitch being connected to the discharge means.

16. The combination as claimed in claim 15, wherein the discharge means is mounted on the container, further comprising a circuit connected to the discharge means and the second switch for activating the former when the latter is activated, the circuit comprising a source of DC power and a relay switch, the second switch when activated closing the relay switch and applying DC power to operate the discharge means.

17. The combination as claimed in claim 16, wherein the discharge means comprises an electromagnetic switch, the DC power source and the relay switch are mounted to the electrosurgical apparatus separate from the pressurized cryogenic fluid container.

18. The combination as claimed in claim 16, wherein the DC power source is part of the electrosurgical apparatus separate from the pressurized cryogenic fluid container, the relay switch is mounted on the pressurized cryogenic fluid container.

19. The combination as claimed in claim 16, further comprising a housing containing at least one of the electrosurgical generator and activating means, and means for mounting the pressurized cryogenic fluid container on the housing.

20. In combination:
(A) electrosurgical apparatus capable of generating electrosurgical currents,
(B) a handpiece having at least a first fingerswitch,
(C) an electrode mounted to the handpiece,
(D) a pressurized cryogenic fluid container,
(E) discharge means connected to the pressurized cryogenic fluid container for causing discharge of cryogenic fluid from the container, the discharge means being mounted on the container,
(F) cryogenic fluid delivery means connected to the pressurized cryogenic fluid container and mounted to the handpiece,
(G) first means for connecting the first fingerswitch to the electrosurgical apparatus such that when the first fingerswitch is activated electrosurgical currents are applied by the electrode to a surgical site to carry out a surgical procedure,
(H) a second switch,
(I) second means for connecting the second switch to the discharge means such that cryogenic fluid released from the pressurized cryogenic fluid container will flow to the fluid delivery means for being applied to the surgical site,
(J) third means for mounting the pressurized cryogenic fluid container containing the relay switch and electromagnetic switch on the handpiece,
(K) the first and second means operating separately and independently, the first and second means comprising first and second fingerswitches, respectively, on the handpiece, the first fingerswitch being connected to the electrosurgical apparatus, the second fingerswitch being connected to the discharge means,
(L) further comprising a circuit connected to the discharge means and the second switch for activating the former when the latter is activated, the circuit comprising a source of DC power and a relay switch, the second switch when activated closing the relay switch and applying DC power to operate the discharge means.

* * * * *